(12) United States Patent
Rivkin

(10) Patent No.: US 8,572,556 B2
(45) Date of Patent: Oct. 29, 2013

(54) GRAPHICALLY BASED METHOD FOR DEVELOPING CONNECTIVITY DRIVERS

(75) Inventor: Slava Rivkin, Ashkelon (IL)

(73) Assignee: Starlims Corporation, Hollywood, FL (US)

( * ) Notice: Subject to any disclaimer, the term of this patent is extended or adjusted under 35 U.S.C. 154(b) by 317 days.

(21) Appl. No.: 12/983,167

(22) Filed: Dec. 31, 2010

(65) Prior Publication Data
US 2012/0174060 A1 Jul. 5, 2012

(51) Int. Cl.
*G06F 9/44* (2006.01)

(52) U.S. Cl.
USPC ........... 717/106; 717/105; 717/109; 717/113; 717/120

(58) Field of Classification Search
USPC .................................. 717/100–120
See application file for complete search history.

(56) References Cited

U.S. PATENT DOCUMENTS

| | | | |
|---|---|---|---|
| 4,812,996 A | 3/1989 | Stubbs | |
| 4,831,580 A | 5/1989 | Yamada | |
| 4,985,857 A | 1/1991 | Bajpai et al. | |
| 5,104,621 A | 4/1992 | Pfost et al. | |
| 5,532,941 A | 7/1996 | Lin | |
| 5,614,415 A | 3/1997 | Markin | |
| 5,664,093 A | 9/1997 | Barnett et al. | |
| 5,812,394 A | 9/1998 | Lewis et al. | |
| 5,920,718 A | 7/1999 | Uczekaj et al. | |
| 5,946,471 A | 8/1999 | Voorhees et al. | |
| 5,985,670 A | 11/1999 | Markin | |
| 6,055,487 A | 4/2000 | Margery et al. | |
| 6,064,812 A | 5/2000 | Parthasarathy et al. | |
| 6,094,684 A | 7/2000 | Pallmann | |
| 6,102,965 A | 8/2000 | Dye et al. | |
| 6,173,438 B1 | 1/2001 | Kodosky et al. | |
| 6,192,320 B1 | 2/2001 | Margrey et al. | |
| 6,219,628 B1 | 4/2001 | Kodosky et al. | |
| 6,298,474 B1 | 10/2001 | Blowers et al. | |
| 6,326,147 B1 | 12/2001 | Oldham et al. | |
| 6,370,569 B1 | 4/2002 | Austin | |
| 6,526,566 B1 | 2/2003 | Austin | |
| 6,581,012 B1 | 6/2003 | Aryev et al. | |
| 6,643,691 B2 | 11/2003 | Austin | |
| 6,681,198 B2 | 1/2004 | Buote et al. | |

(Continued)

OTHER PUBLICATIONS

European Patent Office (International Searching Authority), International Search Report and Written Opinion for PCT/US2011/067706 (Filing Date Dec. 29, 2011) Date of Mailing Apr. 4, 2012.

*Primary Examiner* — Chuck Kendall
(74) *Attorney, Agent, or Firm* — Klintworth & Rozenblat IP LLC

(57) ABSTRACT

A method for graphically developing a connectivity driver is provided. The method includes inputting a hardware message and a first delimiter into computer readable memory medium and generating a first graphical diagram in response. The graphical diagram includes a first branch having a primary parsing node. The first branch represents the discrete record field within the hardware message. The primary parsing node represents the discrete record field within the hardware message and contains information on how to separate the discrete record field from the hardware message. The method also includes graphically assembling a second graphical diagram in response to user input. The second graphical diagram includes a first state node and a second state node. The first state node is connected with the second state node via a transition. The method also includes converting the first and second graphical diagrams into program code from which the connectivity driver is executed.

20 Claims, 16 Drawing Sheets

(56) References Cited

U.S. PATENT DOCUMENTS

| | | |
|---|---|---|
| 6,751,653 B2 | 6/2004 | Austin |
| 6,879,926 B2 | 4/2005 | Schmit et al. |
| 6,909,974 B2 | 6/2005 | Yung et al. |
| 6,938,026 B2 | 8/2005 | Yundt-Pacheco |
| 7,000,191 B2 | 2/2006 | Schmitt et al. |
| 7,162,387 B2 | 1/2007 | Johnson et al. |
| 7,197,418 B2 | 3/2007 | Fuller, III et al. |
| 7,197,743 B2 | 3/2007 | Borg et al. |
| 7,200,838 B2 | 4/2007 | Kodosky et al. |
| 7,275,070 B2 | 9/2007 | Kataria et al. |
| 7,275,235 B2 | 9/2007 | Molinari et al. |
| 7,333,962 B2 | 2/2008 | Zen |
| 7,379,821 B2 | 5/2008 | Yung et al. |
| 7,379,823 B2 | 5/2008 | Yung et al. |
| 7,491,367 B2 | 2/2009 | Yung et al. |
| 7,499,824 B2 | 3/2009 | Johnson et al. |
| 7,506,304 B2 | 3/2009 | Morrow et al. |
| 7,512,931 B2 | 3/2009 | Schmit |
| 7,536,269 B2 | 5/2009 | Sierer et al. |
| 7,565,351 B1 | 7/2009 | Callaghan |
| 7,574,690 B2 | 8/2009 | Shah et al. |
| 7,593,787 B2 | 9/2009 | Feingold et al. |
| 7,593,944 B2 | 9/2009 | Rogers et al. |
| 7,594,220 B2 | 9/2009 | Kodosky et al. |
| 7,594,226 B2 | 9/2009 | Stelzer et al. |
| 7,603,478 B2 | 10/2009 | Thurman et al. |
| 7,603,652 B2 | 10/2009 | Makowski et al. |
| 7,606,950 B2 | 10/2009 | Breyer |
| 7,607,070 B2 | 10/2009 | Clark et al. |
| 7,613,954 B2 | 11/2009 | Grey et al. |
| 7,620,459 B2 | 11/2009 | Renner |
| 7,620,897 B2 | 11/2009 | Shah et al. |
| 7,624,294 B2 | 11/2009 | Conway |
| 7,624,375 B2 | 11/2009 | Santori et al. |
| 7,626,474 B2 | 12/2009 | Mullen et al. |
| 7,627,695 B2 | 12/2009 | Peck et al. |
| 7,627,860 B2 | 12/2009 | Kodosky et al. |
| 7,630,560 B2 | 12/2009 | Wenzel |
| 7,630,854 B2 | 12/2009 | Sierer et al. |
| 7,631,097 B2 | 12/2009 | Moch et al. |
| 7,631,295 B2 | 12/2009 | Makowski et al. |
| 7,644,207 B2 | 1/2010 | Castro et al. |
| 7,647,562 B2 | 1/2010 | Ghercioiu et al. |
| 7,647,578 B2 | 1/2010 | Murphy et al. |
| 7,647,600 B2 | 1/2010 | Muller et al. |
| 7,649,726 B2 | 1/2010 | Castro |
| 7,650,264 B2 | 1/2010 | Kodosky et al. |
| 7,650,316 B2 | 1/2010 | Peck et al. |
| 7,650,574 B2 | 1/2010 | Nattinger |
| 7,650,589 B2 | 1/2010 | Cifra |
| 7,650,594 B2 | 1/2010 | Nattinger |
| 7,668,376 B2 | 2/2010 | Lin et al. |
| 7,669,185 B2 | 2/2010 | Vrancic et al. |
| 7,680,605 B2 | 3/2010 | Yung et al. |
| 7,684,878 B2 | 3/2010 | Reindel et al. |
| 7,689,727 B2 | 3/2010 | Chandhoke |
| 7,689,917 B2 | 3/2010 | Washington et al. |
| RE41,228 E | 4/2010 | Kodosky et al. |
| 7,694,273 B2 | 4/2010 | Kodosky et al. |
| 7,701,869 B2 | 4/2010 | Hogan |
| 7,702,416 B2 | 4/2010 | Ravish et al. |
| 7,702,417 B2 | 4/2010 | Ravish et al. |
| 7,703,027 B2 | 4/2010 | Hsu et al. |
| 7,703,032 B2 | 4/2010 | Wells |
| 7,703,034 B2 | 4/2010 | Kornerup et al. |
| 7,707,014 B2 | 4/2010 | Kodosky et al. |
| 7,725,356 B2 | 5/2010 | Shah et al. |
| 7,725,627 B2 | 5/2010 | Crain, II et al. |
| 7,725,874 B2 | 5/2010 | Kornerup et al. |
| 7,725,877 B2 | 5/2010 | Andrade et al. |
| 7,730,450 B2 | 6/2010 | Mercer |
| 7,743,335 B2 | 6/2010 | Rogers et al. |
| 7,743,362 B2 | 6/2010 | Peck et al. |
| 7,760,238 B2 | 7/2010 | Giesen |
| 7,761,802 B2 | 7/2010 | Shah et al. |
| 7,761,846 B2 | 7/2010 | Hayles |
| 7,761,847 B2 | 7/2010 | Kornerup et al. |
| 7,761,859 B2 | 7/2010 | Low |
| 7,764,619 B2 | 7/2010 | Mathena et al. |
| 7,765,278 B2 | 7/2010 | Dove et al. |
| 7,765,493 B2 | 7/2010 | Chickles et al. |
| 7,769,597 B2 | 8/2010 | Fry et al. |
| 7,778,717 B2 | 8/2010 | Bachman et al. |
| 7,791,671 B2 | 9/2010 | Schultz et al. |
| 7,793,273 B2 | 9/2010 | Mercer et al. |
| 7,801,258 B2 | 9/2010 | Narus et al. |
| 7,802,229 B2 | 9/2010 | Kornerup et al. |
| 2002/0109722 A1 | 8/2002 | Rogers et al. |
| 2002/0111783 A1 | 8/2002 | Kodosky et al. |
| 2002/0174264 A1 | 11/2002 | Fuller et al. |
| 2002/0184326 A1 | 12/2002 | Thomson |
| 2002/0196282 A1 | 12/2002 | Washington et al. |
| 2003/0005179 A1 | 1/2003 | Schmit et al. |
| 2003/0035008 A1 | 2/2003 | Fuller et al. |
| 2003/0036866 A1 | 2/2003 | Nair et al. |
| 2003/0144997 A1 | 7/2003 | Hugley |
| 2003/0145252 A1 | 7/2003 | Grey et al. |
| 2003/0145280 A1 | 7/2003 | Grey et al. |
| 2003/0165259 A1 | 9/2003 | Balent et al. |
| 2003/0172127 A1 | 9/2003 | Northrup et al. |
| 2003/0177042 A1 | 9/2003 | Leon |
| 2003/0177471 A1 | 9/2003 | Chiu et al. |
| 2004/0017392 A1 | 1/2004 | Welch |
| 2004/0031019 A1 | 2/2004 | Lamanna et al. |
| 2004/0032412 A1 | 2/2004 | Odom |
| 2004/0032430 A1 | 2/2004 | Yung et al. |
| 2004/0034478 A1 | 2/2004 | Yung et al. |
| 2004/0039531 A1 | 2/2004 | Yung et al. |
| 2004/0042471 A1 | 3/2004 | Yung et al. |
| 2004/0093180 A1 | 5/2004 | Grey et al. |
| 2004/0122708 A1 | 6/2004 | Avinash et al. |
| 2004/0150667 A1 | 8/2004 | Dove et al. |
| 2004/0205111 A1 | 10/2004 | Chasmawala et al. |
| 2004/0230945 A1 | 11/2004 | Bryant et al. |
| 2005/0022103 A1 | 1/2005 | Yundt-Pacheco |
| 2005/0028107 A1 | 2/2005 | Gomes et al. |
| 2005/0028138 A1 | 2/2005 | Case et al. |
| 2005/0038676 A1 | 2/2005 | Showalter et al. |
| 2005/0049814 A1 | 3/2005 | Ramchandani |
| 2005/0070019 A1 | 3/2005 | Yamamoto |
| 2005/0076002 A1 | 4/2005 | Williams et al. |
| 2005/0106736 A1 | 5/2005 | Yung et al. |
| 2005/0149566 A1 | 7/2005 | Baek et al. |
| 2005/0155014 A1 | 7/2005 | Andrade et al. |
| 2005/0155015 A1 | 7/2005 | Novacek |
| 2005/0177816 A1* | 8/2005 | Kudukoli et al. ............ 717/105 |
| 2005/0195194 A1 | 9/2005 | Cummings |
| 2005/0228608 A1 | 10/2005 | Wells |
| 2005/0257195 A1 | 11/2005 | Morrow et al. |
| 2005/0268173 A1 | 12/2005 | Kudukoli et al. |
| 2006/0008151 A1 | 1/2006 | Lin et al. |
| 2006/0036656 A1 | 2/2006 | Mercer |
| 2006/0036799 A1 | 2/2006 | Shah et al. |
| 2006/0036997 A1 | 2/2006 | Low |
| 2006/0041860 A1 | 2/2006 | Carmichael et al. |
| 2006/0088940 A1 | 4/2006 | Feingold et al. |
| 2006/0117302 A1 | 6/2006 | Mercer et al. |
| 2006/0156294 A1 | 7/2006 | Fuller, III et al. |
| 2006/0168183 A1 | 7/2006 | Fuller, III et al. |
| 2006/0168515 A1 | 7/2006 | Dorsett, Jr. et al. |
| 2006/0190105 A1 | 8/2006 | Hsu et al. |
| 2006/0225034 A1 | 10/2006 | Peck et al. |
| 2006/0291399 A1 | 12/2006 | Mathena et al. |
| 2007/0010911 A1 | 1/2007 | Feingold et al. |
| 2007/0038592 A1 | 2/2007 | Haub et al. |
| 2007/0044030 A1 | 2/2007 | Hayles |
| 2007/0044072 A1 | 2/2007 | Hayles |
| 2007/0044073 A1 | 2/2007 | Kornerup et al. |
| 2007/0044078 A1 | 2/2007 | Cifra |
| 2007/0088865 A1 | 4/2007 | Breyer |
| 2007/0089063 A1 | 4/2007 | Breyer |
| 2007/0129818 A1 | 6/2007 | Andrade et al. |
| 2007/0129894 A1 | 6/2007 | Yung et al. |
| 2007/0141711 A1 | 6/2007 | Stephens et al. |

(56) References Cited

U.S. PATENT DOCUMENTS

| | | |
|---|---|---|
| 2007/0168943 A1 | 7/2007 | Marini et al. |
| 2007/0179644 A1 | 8/2007 | Ravish et al. |
| 2007/0185828 A1 | 8/2007 | Brown |
| 2007/0198445 A1 | 8/2007 | Zen |
| 2007/0214427 A1 | 9/2007 | Peck et al. |
| 2007/0233655 A1 | 10/2007 | Engels |
| 2007/0234195 A1 | 10/2007 | Wells |
| 2007/0244990 A1 | 10/2007 | Wells |
| 2007/0297443 A1 | 12/2007 | Bowers et al. |
| 2008/0022264 A1 | 1/2008 | Macklem et al. |
| 2008/0022270 A1 | 1/2008 | Morrow et al. |
| 2008/0034298 A1 | 2/2008 | Kodosky et al. |
| 2008/0034300 A1 | 2/2008 | Shah et al. |
| 2008/0034345 A1 | 2/2008 | Curtis et al. |
| 2008/0043826 A1 | 2/2008 | Castro et al. |
| 2008/0046414 A1 | 2/2008 | Haub et al. |
| 2008/0052665 A1 | 2/2008 | Bray |
| 2008/0059944 A1 | 3/2008 | Patterson et al. |
| 2008/0240321 A1 | 10/2008 | Narus et al. |
| 2008/0256511 A1 | 10/2008 | Lay et al. |
| 2008/0263343 A1 | 10/2008 | Kassas et al. |
| 2008/0263512 A1 | 10/2008 | Dellas et al. |
| 2008/0263515 A1 | 10/2008 | Dellas et al. |
| 2008/0263521 A1 | 10/2008 | Neumann et al. |
| 2008/0270920 A1 | 10/2008 | Hudson |
| 2008/0300697 A1 | 12/2008 | Moriat et al. |
| 2008/0307332 A1 | 12/2008 | Hayles et al. |
| 2009/0019453 A1 | 1/2009 | Kodaganur et al. |
| 2009/0027509 A1 | 1/2009 | Giesen |
| 2009/0049424 A1 | 2/2009 | Kumar et al. |
| 2009/0089715 A1 | 4/2009 | Dickey |
| 2009/0106755 A1 | 4/2009 | Chandhoke |
| 2009/0106761 A1 | 4/2009 | Chandhoke |
| 2009/0113322 A1 | 4/2009 | Rogers |
| 2009/0113337 A1 | 4/2009 | Rogers |
| 2009/0121908 A1 | 5/2009 | Regier |
| 2009/0130765 A1 | 5/2009 | Bauer et al. |
| 2009/0178025 A1 | 7/2009 | Morrow et al. |
| 2009/0193396 A1 | 7/2009 | Hartadinata |
| 2009/0234471 A1 | 9/2009 | Chandhoke |
| 2009/0235231 A1 | 9/2009 | Kodosky et al. |
| 2009/0241068 A1 | 9/2009 | Page et al. |
| 2009/0241069 A1 | 9/2009 | Fuller, III et al. |
| 2009/0288025 A1 | 11/2009 | King et al. |
| 2009/0288073 A1 | 11/2009 | Gosalia et al. |
| 2009/0292511 A1 | 11/2009 | Vrancic et al. |
| 2009/0293044 A1 | 11/2009 | Boettcher et al. |
| 2009/0297042 A1 | 12/2009 | Nair et al. |
| 2009/0299924 A1 | 12/2009 | Bauer et al. |
| 2009/0319987 A1 | 12/2009 | Bartz |
| 2010/0010646 A1 | 1/2010 | Drew et al. |
| 2010/0023866 A1 | 1/2010 | Peck et al. |
| 2010/0030509 A1 | 2/2010 | Crain, II et al. |
| 2010/0030539 A1 | 2/2010 | Chandhoke et al. |
| 2010/0031231 A1 | 2/2010 | Ilic et al. |
| 2010/0058289 A1 | 3/2010 | Hudson, III et al. |

* cited by examiner

```
Leeton|||||||||Decatur|rh|0|1|UNK|UNK^A100^||^^^1003^Cl^DIL1^P|R||20020719141900|||||||||||F|r\nR|1|^^^1003^Cl^DIL1^P^^^^F|9
8.7|UG/L|2 to 1000|||||R|Ken Nash||20020923080000|5\r\nCl|||Every thing looks great!|G|r\nR|2|^^^1003^Cl^DIL1^P^^^^||500|||||R|Ken
Nash||20020923080000|5\r\nR|3|^^^1003^Cl^DIL1^P^^^^P|50|RLU|||||R||Ken Nash||20020923080000|5\r\nL|1"
    </InstrumentDetails>
    <TransmisionDetails>
        <ColLevel1>
            <Content message="H position=0 field="header"/>
            <ColLevel2>
                <Content message="^&" position=1 field="init"/>
                <Content message=""""^4^800A^H1P1O1R1C1Q1L1" position=4 field="deviceId"/>
                <Content message="P" position=11 field=""/>
                <Content message="1" position=12 field=""/>
                <Content message="20090414134122" position13 field=""" />
            </ColLevel2>
            <Content message="P" position=1 field="patientDetails"/>
            <ColLevel2>
                <Content message="1" position=1 field=""/>
                <Content message="1" position=2 field=""/>
                <Content message="2" position=3 field=""/>
                <Content message="6" position=4 field=""/>
                <Content message="P" position=5 field=""/>
                <Content message="Spence^Randy^W." position=6 field="name"/>
                <Content message="19611127" position=8 field=""/>
```

Fig.2B

GRAPHICALLY BASED METHOD FOR DEVELOPING CONNECTIVITY DRIVERS

FIELD OF THE INVENTION

The present invention relates generally a method for developing communication drivers. In particular, the invention relates to a graphically based method for developing connectivity drivers.

BACKGROUND

A Laboratory Information Management System or Laboratory Integration Management Solution (LIMS) is a software system used in laboratories for the integration of laboratory software and instruments and the management of samples, laboratory users, standards and other laboratory functions such as Quality Assurance (QA) and Quality Control (QC), sample planning, invoicing, plate management, and workflow automation. LIMS implementations may also support information gathering, decision making, calculation, review and release into the workplace and away from the office. More recently, LIMS products are starting to expand into Electronic Laboratory Notebooks, assay data management, data mining and data analysis.

One core function of LIMS is the management of samples. This typically is initiated when a sample is received in the laboratory at which point the sample will be registered in the LIMS. This registration process may involve accessioning the sample and producing barcodes to affix to the sample container. Various other parameters may be recorded as well, such as clinical or phenotypic information corresponding with the sample. The LIMS may then track chain of custody of the sample as well as the sample location. Location tracking often involves assigning the sample to a particular location such as a shelf/rack/box/row/column. Other event tracking may be required such as freeze and thaw cycles that a sample undergoes in the laboratory.

Modern LIMS have implemented extensive configurability as each laboratories needs for tracking additional data points can vary widely. LIMS vendors often cannot make assumptions about what these data tracking needs are and therefore need to be adaptable to each environment. LIMS users may also have regulatory concerns to comply with such as CLIA, HIPAA, GLP and FDA specifications and this can affect certain aspects of sample management in a LIMS solution. One key to compliance with many of these standards is audit logging of all changes to LIMS data, and in some cases a full electronic signature system is required for rigorous tracking of field level changes to LIMS data.

One may configure a LIMS whereby users are assigned roles or groups. Typically the role of a user will dictate their access to specific data records in the LIMS. Each user account is protected by security mechanisms such as a user id and a password. Users may have customized interfaces based on their role in the organization. For example, a laboratory manager might have full access to all of a LIMS functions and data, whereas technicians might have access only to data and functionality needed for their individual work-tasks.

Some LIMS offer some capability for integration with instruments. A LIMS may create control files that are "fed" into the instrument and direct its operation on some physical item such as a sample tube or sample plate. The LIMS may then import instrument results files to extract QC or results data for assessment of the operation on the sample or samples. Data owners may access the resulting stored information at any time.

In order to communicate between the LIMS and an instrument, a device driver, also known as a connectivity driver, may be used. A connectivity driver is a computer program allowing a higher-level computer program, such as the LIMS, to interact with a hardware device, such as an instrument. A connectivity driver typically communicates with the hardware device through a system bus of a computer or a communications device connected with the computer, such as a radio or a network interface to which the hardware device connects. When a higher-level computer program invokes a routine in the connectivity driver, the connectivity driver issues commands to the hardware device. If the hardware device sends data back to the connectivity driver, the connectivity driver may invoke routines in the higher-level computer program and may translate and transfer information received by the hardware device into a format which can be read and used by the higher-level computer program. Connectivity drivers are often hardware-dependent and specific to the higher-level computer program. Connectivity drivers also usually provide interrupt handling required for any necessary asynchronous time-dependent interface between the hardware device and the higher-level computer program.

When developing a connectivity driver for a LIMS, a user typically has to write program code for a computer program from which the connectivity driver is executed for each hardware device for which the LIMS wishes to communicate and interact with. The task of writing program code for a connectivity driver is often laborious and requires many hours of work from a trained computer programmer to complete. Writing program code for a connectivity driver also requires an in-depth understanding of how the hardware device and the higher-level computer program function. Typically, the user of a LIMS does not have the type of training and skills needed to write the program code needed from which the connectivity driver is executed. Thus the task of writing program code for a connectivity driver usually falls to a software engineer.

It would be desirable to provide a simplified method for developing connectivity drivers which does not require the use of a software engineer. It would also be desirable to provide a simplified method for developing connectivity drivers from which an end-user could develop program code for a connectivity driver.

SUMMARY

In one aspect, a computer readable memory medium comprising program instructions for graphically developing a connectivity driver is provided. The program instructions are executable by a processor to assemble a first graphical diagram in response to user input. The first graphical diagram represents a parsing sequence for analyzing and converting a hardware message sent using a hardware protocol into software data having a file format readable by a computer program. The entire parsing sequence defines a hardware grammar used to encode and decode discrete fields into and from the hardware message. The first graphical diagram includes a first branch having a primary parsing node. The primary parsing node represents a discrete record field within the hardware message and contains information on how to separate the discrete record field from the hardware message. The program instructions are also executable by a processor to assemble a second graphical diagram in response to user input. The second graphical diagram includes a first state node and a second state node. The first state node is connected with the second state node via a transition. Each state node represents a unique hardware state of the hardware device. The transition includes a transition condition required to move from the first state to the second state. The second graphical diagram maps out various states of the hardware device. The program instructions are also executable by a processor to convert the first and second graphical diagrams into program code from which the connectivity driver is executed.

In one aspect, a method for graphically developing a connectivity driver is provided. The method includes inputting a hardware message having a stream of data into a computer readable memory medium. The hardware message has a first delimiter for demarking the boundary of a discrete record field within the hardware message. The method also includes inputting the first delimiter into the computer readable memory medium. The method also includes accessing the computer readable memory medium and generating, using a processor, a first graphical diagram in response to the inputting of the first delimiter. The graphical diagram includes a first branch having a primary parsing node. The first branch represents the discrete record field within the hardware message. The primary parsing node represents the discrete record field within the hardware message and contains information on how to separate the discrete record field from the hardware message. The method also includes graphically assembling a second graphical diagram in response to user input. The second graphical diagram includes a first state node and a second state node. The first state node is connected with the second state node via a transition. Each state node represents a unique hardware state of the hardware device. The transition includes a transition condition required to move from the first state to the second state. The second graphical diagram maps out various states of the hardware device. The method also includes converting the first and second graphical diagrams into program code from which the connectivity driver is executed.

In one aspect, a laboratory information management system for documenting an evidence packaging structure is provided. The system includes a computer readable memory medium and at least one processor operable to access from the computer readable memory medium program instructions executable by the processor. The program instructions are executable by the processor to assemble a first graphical diagram in response to user input. The first graphical diagram represents a parsing sequence for analyzing and converting a hardware message sent using a hardware protocol into software data having a file format readable by a computer program. The entire parsing sequence defines a hardware grammar used to encode and decode discrete fields into and from the hardware message. The first graphical diagram includes a first branch having a primary parsing node. The primary parsing node represents a discrete record field within the hardware message and contains information on how to separate the discrete record field from the hardware message. The program instructions are also executable by the processor to assemble a second graphical diagram in response to user input. The second graphical diagram includes a first state node and a second state node. The first state node is connected with the second state node via a transition. Each state node represents a unique hardware state of the hardware device. The transition includes a transition condition required to move from the first state to the second state. The second graphical diagram maps out various states of the hardware device.

The scope of the present invention is defined solely by the appended claims and is not affected by the statements within this summary.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

The present invention makes use of the discovery that by providing a user with software which can generate a first graphical diagram which represents a parsing sequence to parse a hardware message into a software message and a second graphical diagram which represents hardware states of a hardware device, program code for a connectivity driver can be generated without requiring the use of a software engineer, providing a means for users to more simply and easily generate connectivity drivers.

In the description that follows, the subject matter of the application will be described with reference to acts and symbolic representations of operations that are performed by one or more computers, unless indicated otherwise. As such, it will be understood that such acts and operations, which are at times referred to as being computer-executed, include the manipulation by the processing unit of the computer of electrical signals representing data in a structured form. This manipulation transforms the data or maintains it at locations in the memory system of the computer which reconfigures or otherwise alters the operation of the computer in a manner well understood by those skilled in the art. The data structures where data is maintained are physical locations of the memory that have particular properties defined by the format of the data. However, although the subject matter of the application is being described in the foregoing context, it is not meant to be limiting as those skilled in the art will appreciate that some of the acts and operations described hereinafter can also be implemented in hardware, software, and/or firmware and/or some combination thereof.

Figure 1:
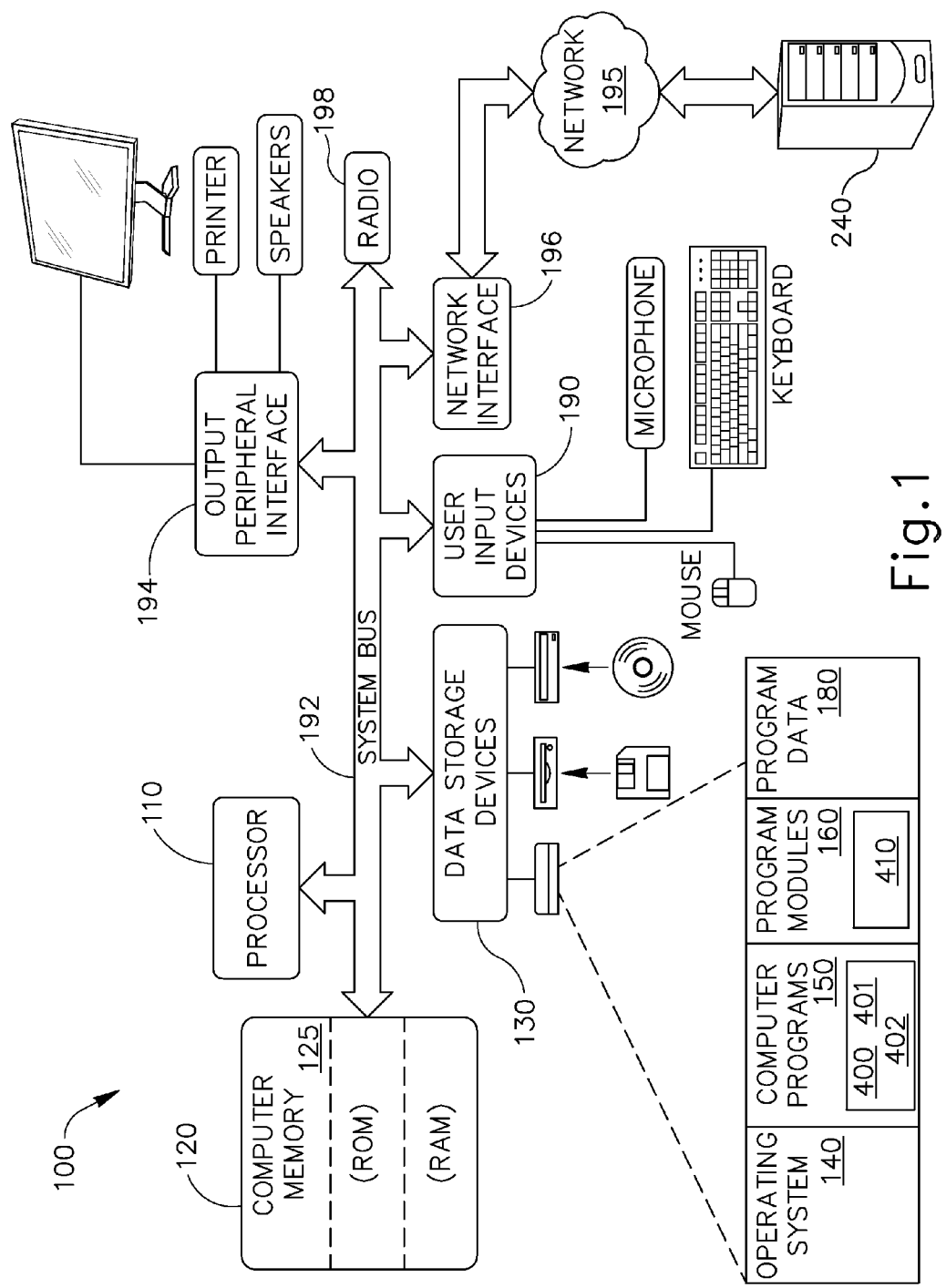
FIG. 1 depicts a block schematic diagram of an exemplary computing system, in accordance with one embodiment of the present invention.

With reference to FIG. 1, depicted is an exemplary computing system for implementing embodiments. FIG. 1 includes computer 100 running a computer program, such as a LIMS software application 400, a laboratory information system (LIS) software application 401, or a middleware program 402. The LIMS software 400 is a software system used in laboratories for the integration of laboratory software and instruments and the management of samples, laboratory users, standards and other laboratory functions such as Quality Assurance (QA) and Quality Control (QC), sample planning, invoicing, plate management, and workflow automation. The LIS software application 401 is a class of software that receives, processes, and stores information generated by medical laboratory processes. The LIS software application 401 often must interface with instruments and other information systems such as hospital information systems (HIS). The LIS software application 401 is a highly configurable application which is customized to facilitate a wide variety of laboratory workflow models. A middleware program 402 is a piece of software that operates between a first computer program, such as a LIMS software application 400 or a LIS software application 401, and a hardware device 200.

The computer 100 includes a processor 110 in communication with a computer readable memory medium 120. Computer readable memory medium 120 is any medium which can be used to store information which can later be accessed by processor 110. Computer readable memory medium 120 includes computer memory 125 and data storage devices 130. Computer memory 120 is preferably a fast-access memory and is used to run program instructions executable by the processor 110. Computer memory 120 includes random access memory (RAM), flash memory, and read only memory (ROM). Data storage devices 130 are preferably physical devices and are used to store any information or computer program which may be accessed by the processor 110, such as an operating system 140, computer programs 150 such as LIMS software application 400, program modules 160 such as a driver development module 410 which runs as a part of LIMS software application 400, and program data 180. Data storage devices 130 and their associated computer readable memory medium provide storage of computer readable instructions, data structures, program modules and other data for the computer 100. Data storage devices 130 include magnetic medium like a floppy disk, a hard disk drive, and magnetic tape; an optical medium like a Compact Disc (CD), a Digital Video Disk (DVD), and a Blu-ray Disc; and solid state memory such as random access memory (RAM), flash memory, and read only memory (ROM).

Computer 100 further includes input devices 190 through which data may enter the computer 100, either automatically or by a user who enters commands and data. Input devices 190 can include an electronic digitizer, a flatbed scanner, a barcode reader, a microphone, a camera, a video camera, a keyboard and a pointing device, commonly referred to as a mouse, a trackball or a touch pad, a pinpad, any USB device, any Bluetooth enabled device, an RFID or NFC device, and a debit card reader. Other input devices may include a joystick, game pad, satellite dish, scanner, an instrument, a sensor, and the like. In one or more embodiments, input devices 190 are portable devices that can direct display or instantiation of applications running on processor 110.

These and other input devices 190 can be connected to processor 110 through a user input interface that is coupled to a system bus 192, but may be connected by other interface and bus structures, such as a parallel port, game port or a universal serial bus (USB). Computers such as computer 100 may also include other peripheral output devices such as speakers, printers, and/or display devices, which may be connected through an output peripheral interface 194 and the like.

Computer 100 also includes a radio 198 or other type of communications device for wirelessly transmitting and receiving data for the computer 100 with the aid of an antenna. Radio 198 may wirelessly transmit and receive data using WiMAX™, 802.11a/b/g/n, Bluetooth™, 2G, 2.5G, 3G, and 4G, wireless standards.

Computer 100 may operate in a networked environment 195 using logical connections to one or more remote computers, such as a remote server 240. The remote server 240 may be a personal computer, a server, a router, a network PC, a peer device or other common network node, and may include many if not all of the elements described above relative to computer 100. Networking environments are commonplace in offices, enterprise-wide computer networks, intranets and the Internet. For example, in the subject matter of the present application, computer 100 may comprise the source machine from which data is being migrated, and the remote computer may comprise the destination machine. Note, however, that source and destination machines need not be connected by a network or any other means, but instead, data may be migrated via any media capable of being written by the source platform and read by the destination platform or platforms. When used in a LAN or WLAN networking environment, computer 100 is connected to the LAN or WLAN through a network interface 196 or an adapter. When used in a WAN networking environment, computer 100 may include a modem or other means for establishing communications over the WAN, such as radio 198, to environments such as the Internet or to another remote computer. It will be appreciated that other means of establishing a communications link between computer 100 and other remote computers may be used.

In one embodiment, computer 100 is in communication with remote server 240, and the LIMS software application 400 is run on the remote server 240, receiving commands and information from the computer 100 being input by a user. Information from the LIMS software application 400 running on the remote server 240 is displayed on a display connected with the computer 100.

Figure 2A:
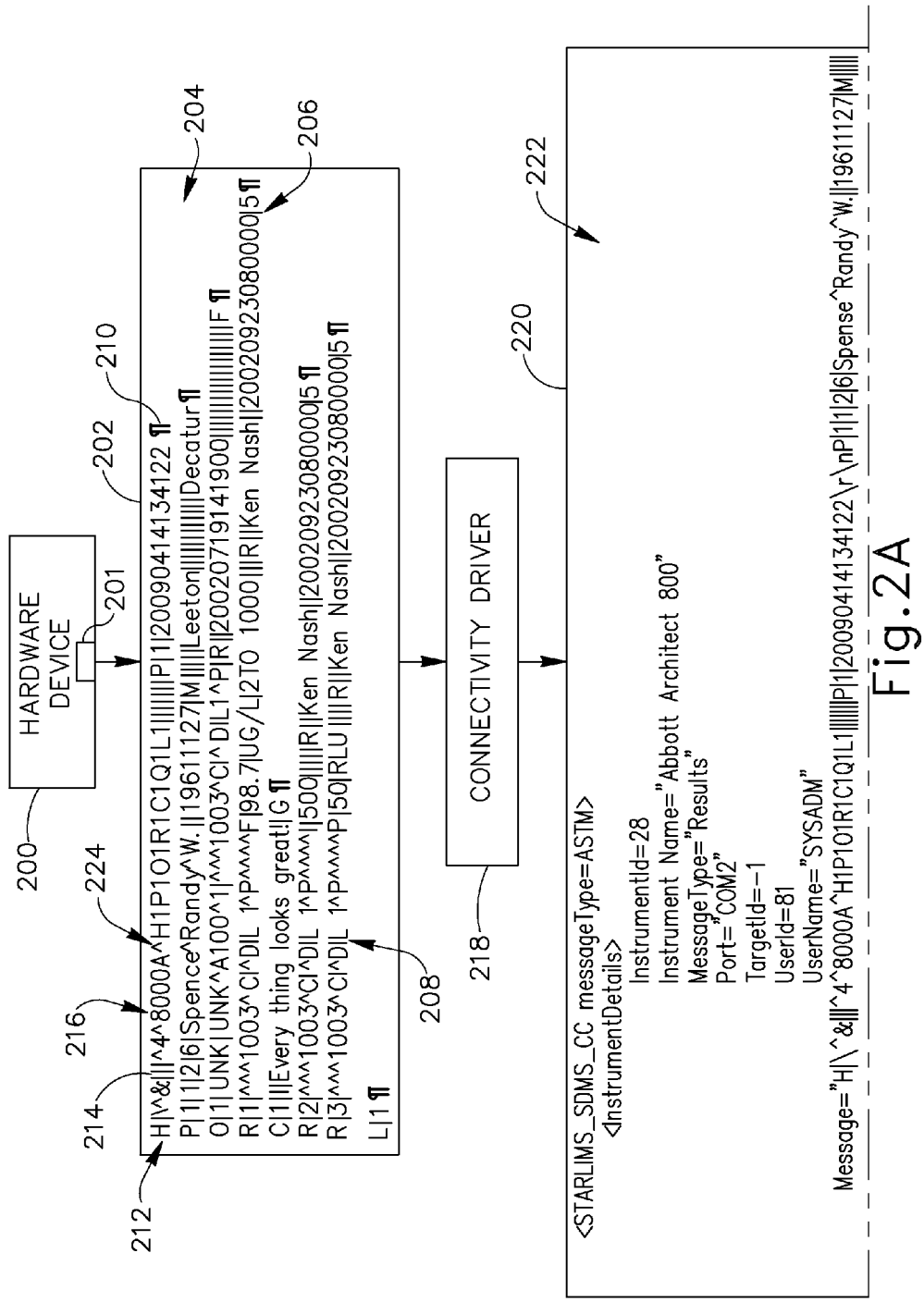
FIG. 2 depicts an illustration of a connectivity driver receiving a hardware message from a hardware device and converting the hardware message into software data, in accordance with one embodiment of the present invention.
Figure 2C:
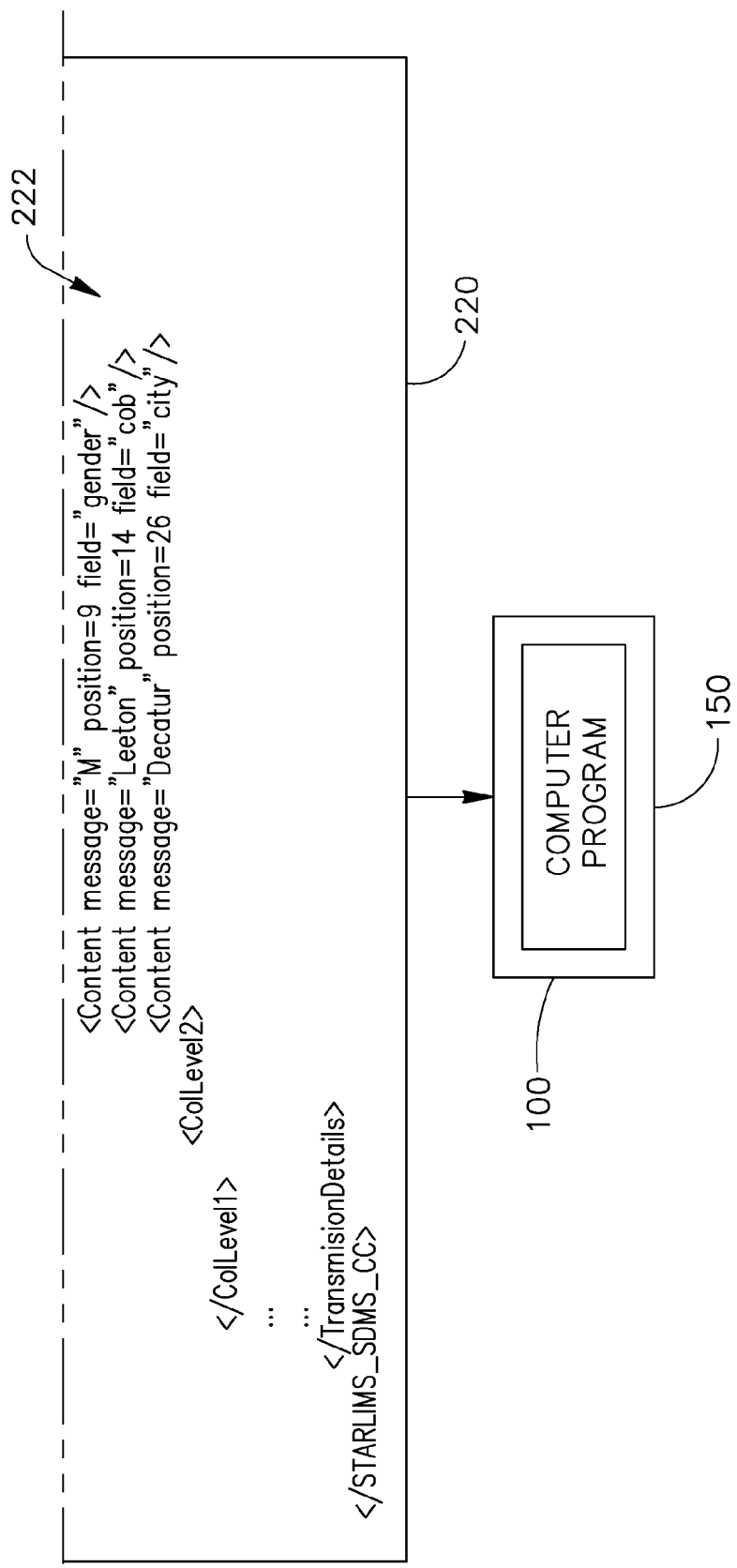

With reference to FIG. 2, a hardware device 200 generates a hardware message 202 which is communicated to a computer program 150 residing on computer 100 or a computer program 150 residing on remote server 240. The hardware device 200 is any piece of electronic hardware having a communications interface 201, such as a radio 198, a network interface 196, or an output peripheral interface 194 which can communicate with an interface with another 192 piece of electronic hardware, also having a communications interface. Preferably, hardware device 200 is any instrument, computer, or piece of electronic hardware found in a laboratory which can transmit and output the hardware message 202 to another instrument, computer 100, or piece of electronic hardware. In one embodiment, hardware device 200 is a laboratory instrument for use in a clinical laboratory, which many be used to analyze mammalian biological samples.

Hardware device 200 generates and outputs the hardware message 202 via communications interface 201. Hardware message 202 is encoded using a hardware protocol 204 used to encode discrete fields 208 of data using delimiters 206 for demarking the boundary of a discrete field 208 within the hardware message 202. Protocol 204 can be any standard on non-standard protocol used to encode information by a hardware device, such as HL7, ASTM, File buffers, or other custom protocols defined by a manufacturer of a hardware device 200. Delimiters 206 can be any type of textual character, symbols, binary structures, position information, or mark and includes such characters as: "~", "|", "\", "[", "]", "^", and a paragraph mark, for example. Instead of relying on a specific character or symbol, position information relies on a specific position within the hardware message 202 to delimit the hardware message 202. Additionally, mark relies on a demarcation within the hardware message 202, such as an end-of-line indicator or section break, to delimit the hardware message 202.

In one embodiment, the hardware message 202 includes record delimiters 210, field delimiters 214, and bracket delimiters 224. Field delimiters 214 separate discrete data fields 216 and record delimiters 210 separate groups of discrete data fields 216 known as a discrete record field 212. For example, a comma-separated values (CSV) file format uses a comma as a field delimiter 214 between discrete data fields 216, and an end-of-line indicator, or paragraph mark, as a record delimiter 210 between discrete record fields 212. Bracket delimiters 224, also known as block delimiters, region delimiters or balanced delimiters, mark both the start and end of a discrete region of text 226 within discrete data fields 216. For example, discrete data fields 216 may include information such as a Patient's Name, wherein the first, last and middle names of the patient may be separated using a bracket delimiter 224.

Figure 12:
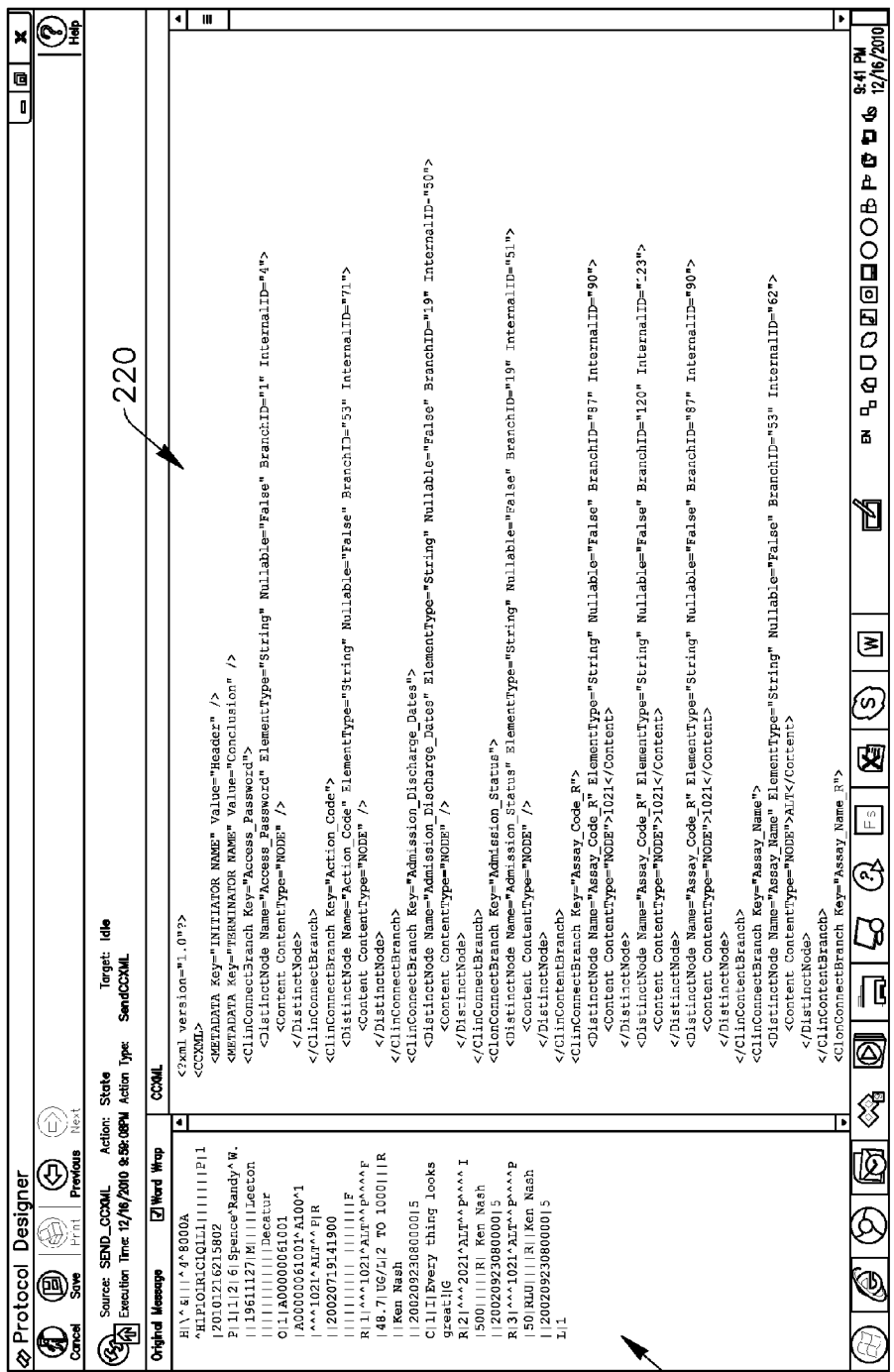
FIG. 12 depicts the contents of a hardware message and the corresponding software data, in accordance with one embodiment of the present invention.
Figure 13A:
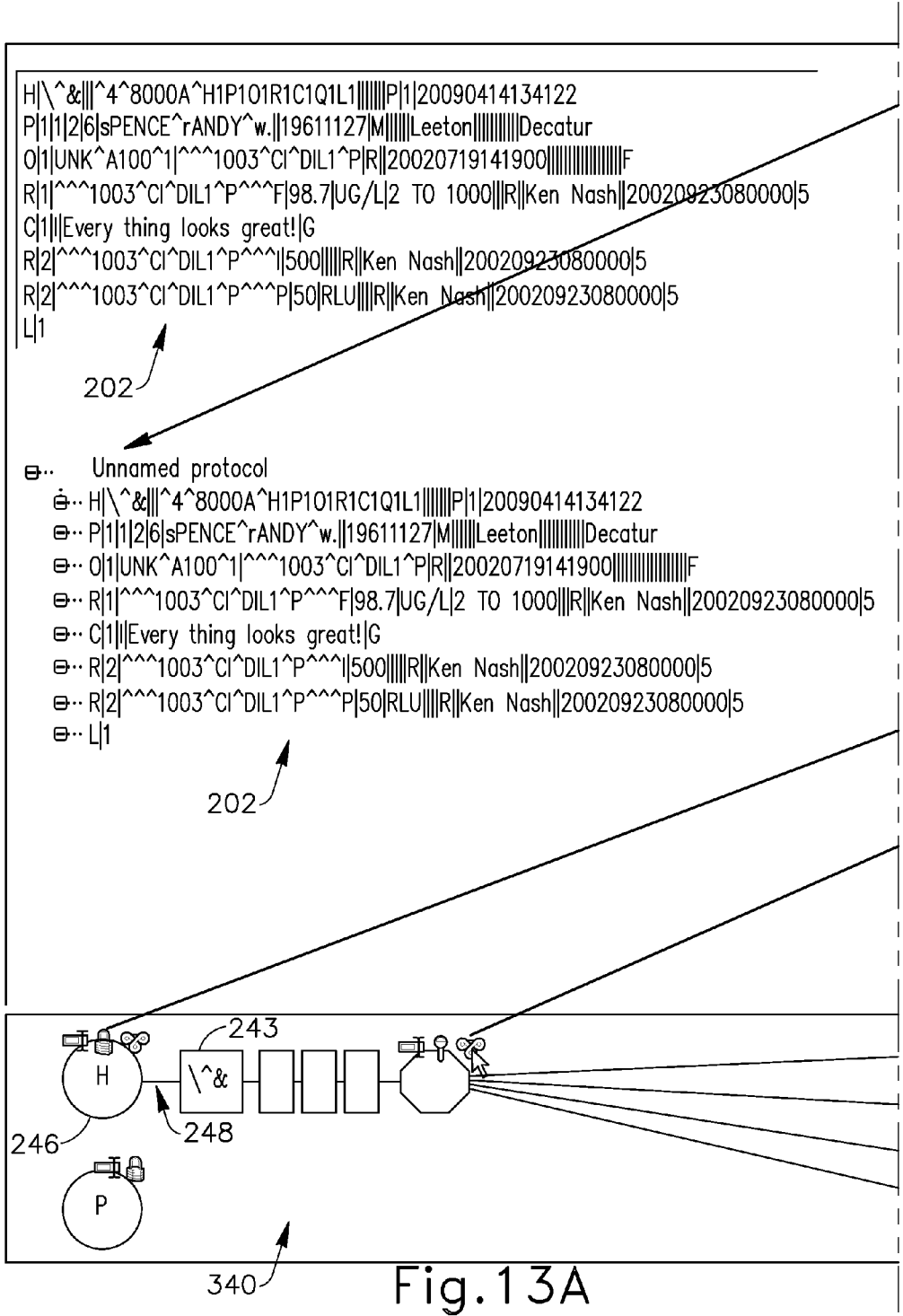
FIG. 13 depicts a first graphical diagram used to generate a connectivity driver and the corresponding software data and hardware message represented by the first graphical diagram, in accordance with one embodiment of the present invention.
Figure 13B:
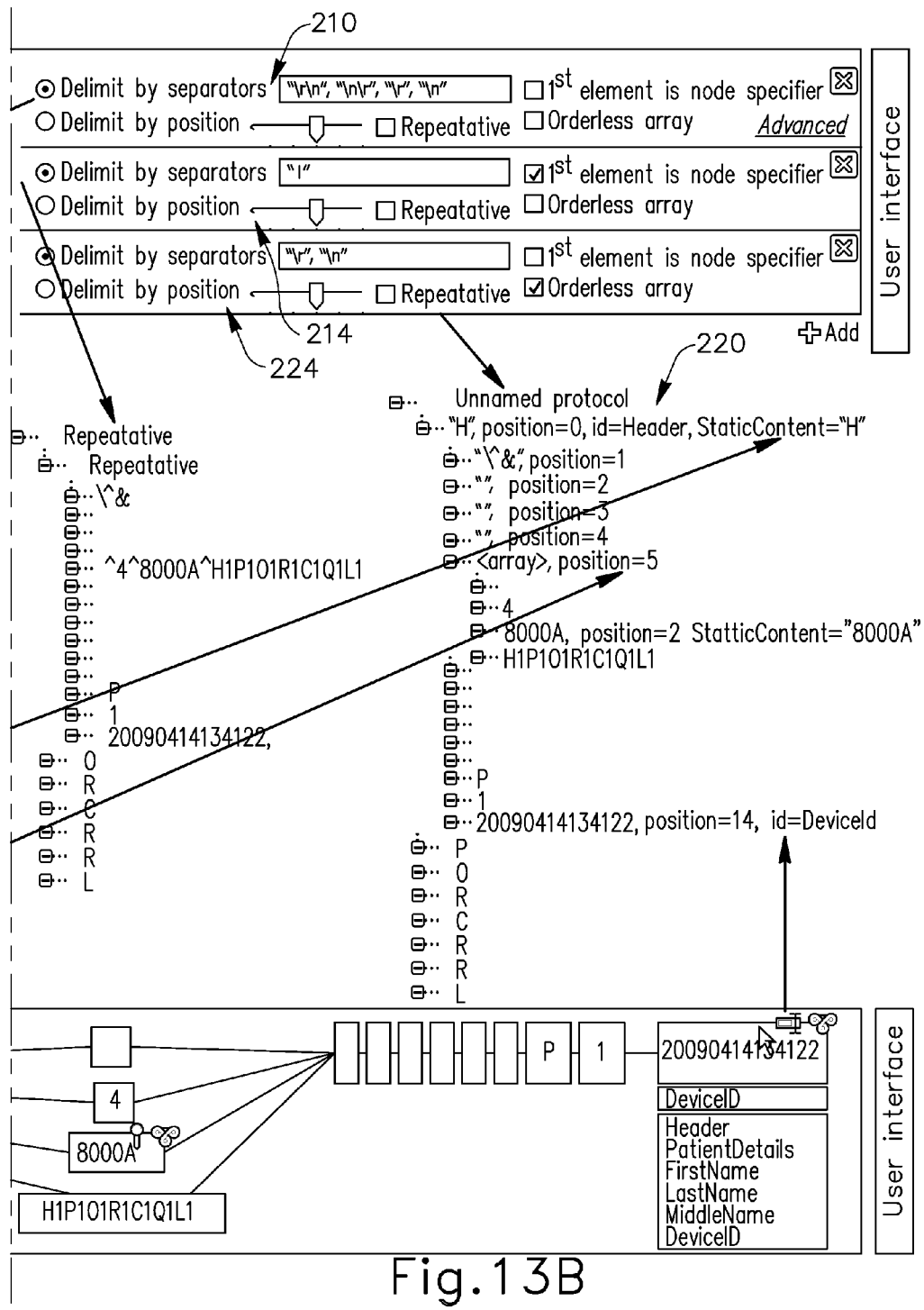

Upon outputting the hardware message 202 via communications interface 201, the hardware message 202 is received by a connectivity driver 218, having a parsing sequence for analyzing and converting the hardware message 202 sent using the hardware protocol 204 into software data 220 having a file format 222 readable by computer program 150, wherein the entire parsing sequence defines a hardware grammar used to encode and decode discrete fields 208 into and from the hardware message 202. The connectivity driver 218 also uses the parsing sequence for analyzing and converting the software data 220 having the file format 222 into the hardware message 202 sent using hardware protocol 204, which is readable by hardware device 200. With reference to FIGS. 12-13, the connectivity driver 218 serves to essentially translate hardware messages 202 into software data 220 and software data 220 into hardware messages 202, so that the hardware device 200 can communicate with the computer program 150 within computer 100 or remote server 240, and so that the computer program 150 can communicate with the hardware device 200. Software data 220 may use any file format 222 readable by computer program 150, such as XML.

Figure 3:
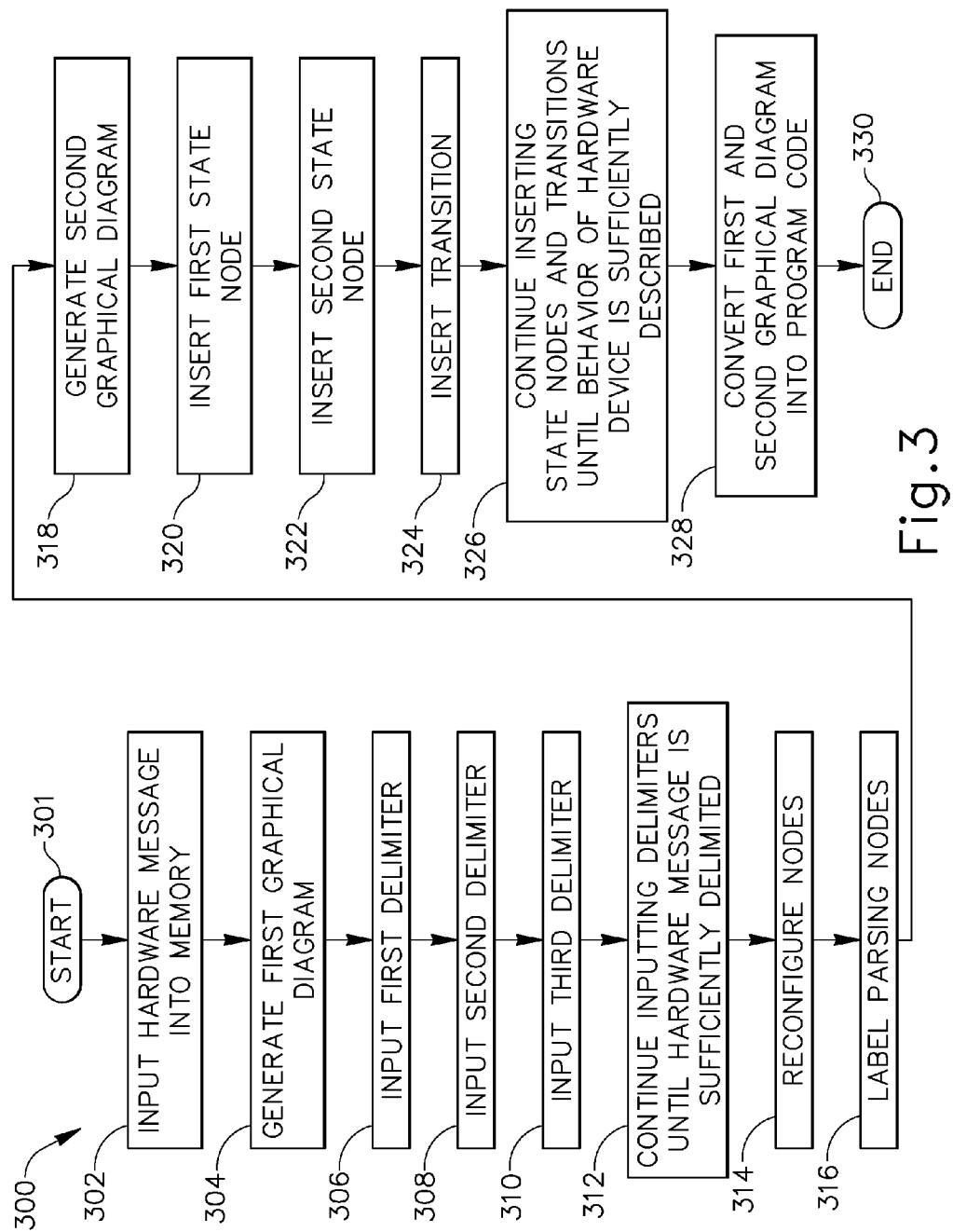
FIG. 3 depicts flowchart illustrations of methods, apparatus (systems) and computer program products, in accordance with one embodiment of the present invention.

With reference to FIG. 3, is a flowchart representation of a method 300 for graphically developing a connectivity driver 218. Method 300 is initiated at block 301 by launching LIMS software application 400 within the computer 100 or the remote server 240. Preferably, concurrent with the launching of computer program 150, driver development module 230 is also launched which preferably resides within the computer program 150. However, driver development module 230 may be a separate program which is not embedded within computer program 150 or launched concurrently with computer program 150. Moving to block 302, upon launching the driver development module 230, a hardware message 202 having a stream of data is input into computer readable memory medium 120 and provided to driver development module 230. The hardware message 202 may be an actual hardware message 202 or a sample hardware message 203 formatted to simulate an actual hardware message 202. The sample hardware message 203 is encoded using the same hardware protocol 204 as hardware message 202. Hardware message 202 is used to provide the user with a template for instructing the driver development module 230 on how to parse the hardware message 202 encoded using hardware protocol 204.

Figure 4:
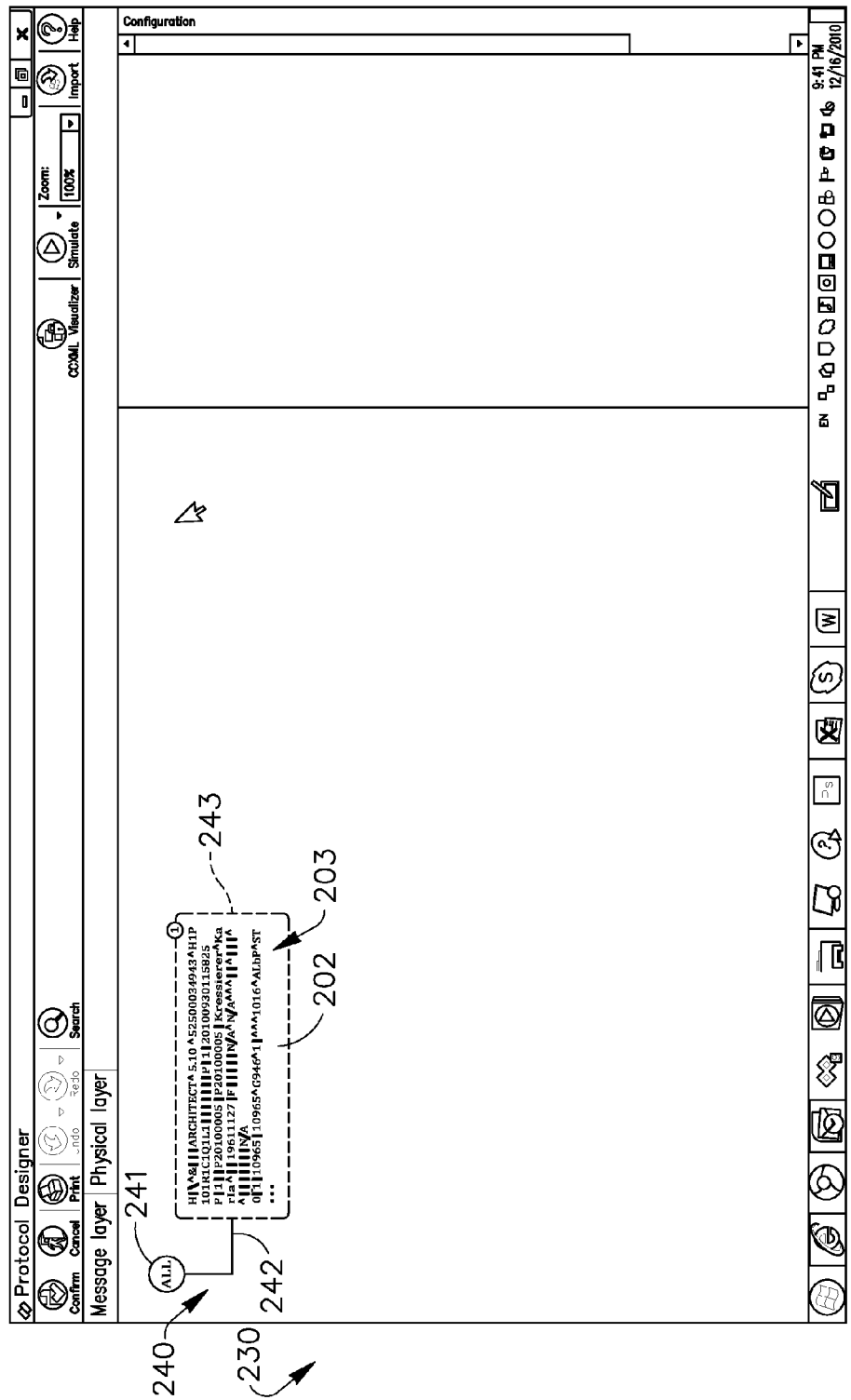
FIGS. 4-9 depict various states of a first graphical diagram used to generate a connectivity driver, in accordance with one embodiment of the present invention.

With reference to FIG. 4, upon inputting the hardware message 202, the driver development module 230 generates a first graphical diagram 240 having a root node 241 connected to an initial global branch or first branch 242 having an initial parsing node 243 at block 304. The initial parsing node 243 represents the entire contents of hardware message 202.

Moving to block 306, the user then inputs a first delimiter 232 into the computer readable memory medium 120. The first delimiter 232 helps to modify first graphical diagram 240 and further generate additional parsing nodes 243 within the first graphical diagram 240. Each parsing node 243 represents a discrete field 208 of data within the message header 202.

Figure 5:
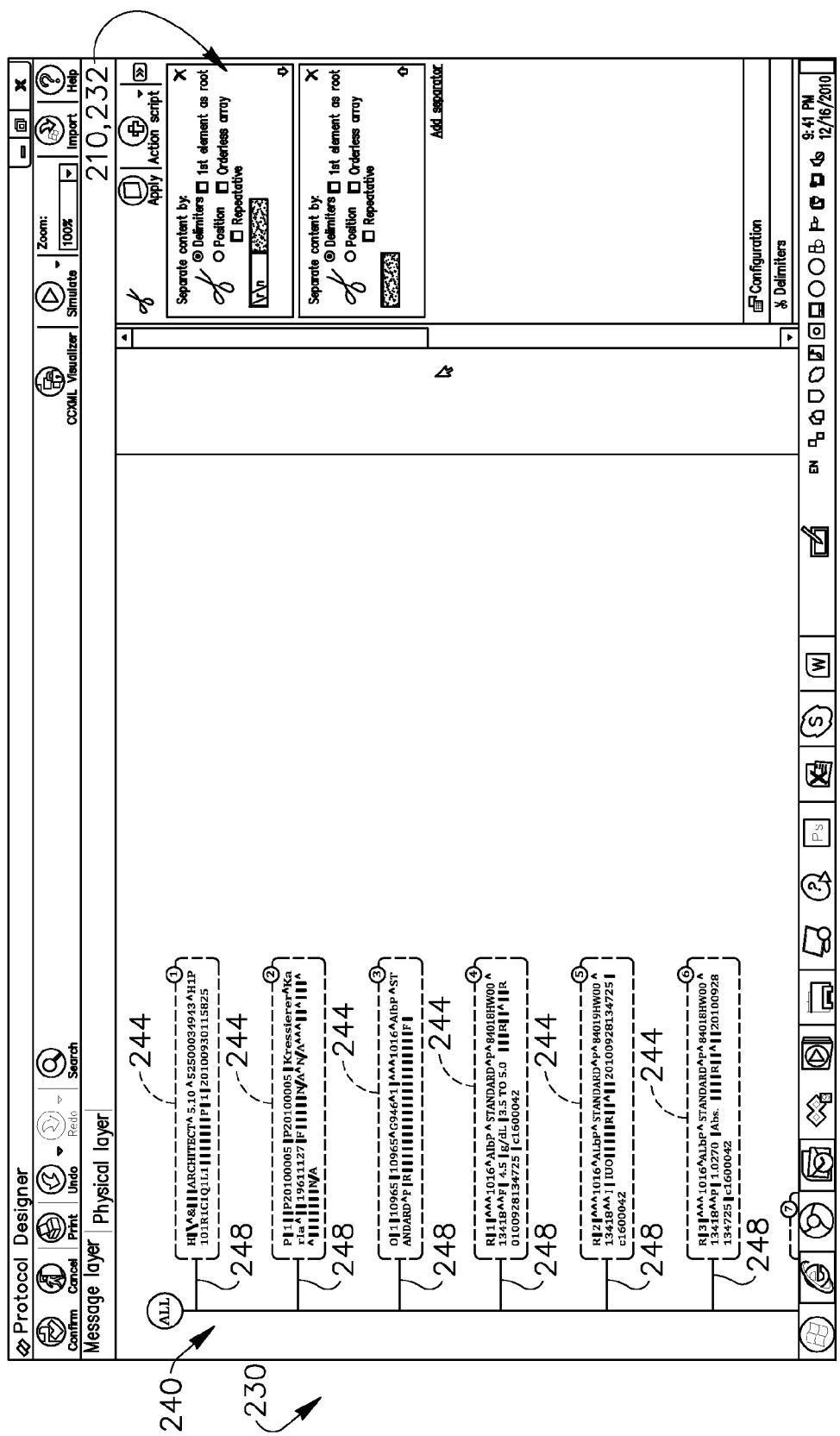

In one embodiment, the first delimiter 232 is a record delimiter 210. With reference to FIG. 5, if the first delimiter 232 is a record delimiter 210, the hardware message 202 is delimited into discrete record fields 212 and the driver development module 230 generates in the first graphical program 240 a branch 248 having a primary parsing node 244 for each discrete record field 212 of the hardware message 202 which is delimited using the first delimiter 232. Each branch 248 represents each discrete record field 212 of the hardware message 202. Each primary parsing node 244 represents the discrete record field 212 within the hardware message 202 and contains delimiting information on how to separate and delimit the discrete record field 212 from the hardware message 202. Delimiting information may include the recorder delimiter 210 or record delimiters 210 used to delimit the discrete record field 212 from the hardware message 202.

Moving to block 308, the user then inputs a second delimiter 234 into the computer readable memory medium 120. The second delimiter 234 helps to modify first graphical diagram 240 and further generate additional parsing nodes 243 within the first graphical diagram 240. Each parsing node 243 represents a discrete field 208 of data within the message header 202.

Figure 6:
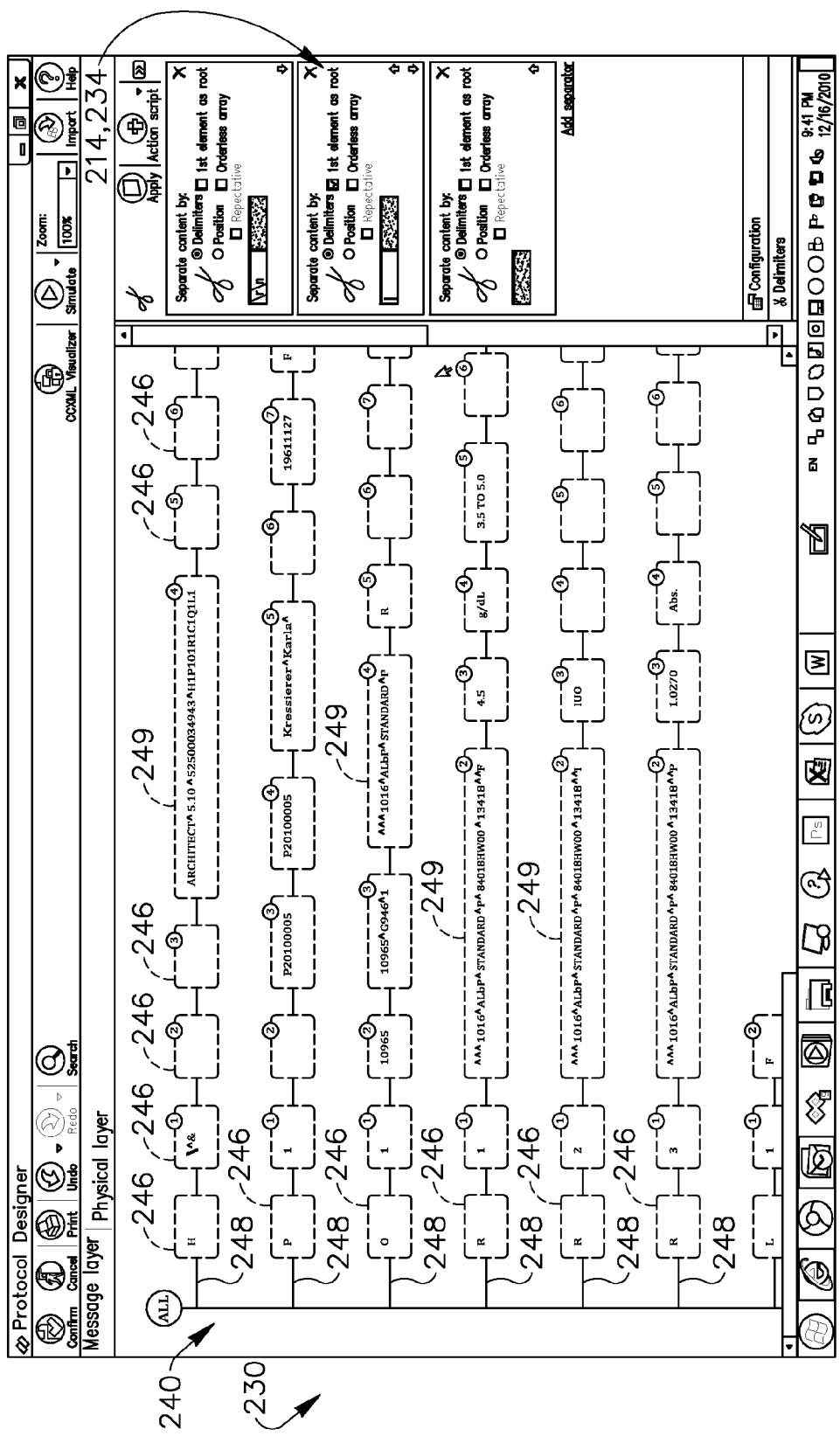

In one embodiment, the second delimiter 234 is a field delimiter 214. With reference to FIG. 6, if the second delimiter 234 is a field delimiter 214, the hardware message 202 is further delimited into discrete data fields 216 and the driver development module 230 generates in the first graphical program 240 additional parsing nodes 246 for each discrete data field 216 of the hardware message 202 which is delimited using the second delimiter 234. Each additional parsing node 246 represents a discrete data field 216 of the hardware message 202 and contains delimiting information on how to separate and delimit the discrete data field 216 from the hardware message 202. Delimiting information may include the field delimiter 214 or field delimiters 214 used to delimit the discrete data field 216 from the hardware message 202.

Moving to block 310, the user then inputs a third delimiter 236 into the computer readable memory medium 120. The third delimiter 236 helps to modify first graphical diagram 240 and further generate additional parsing nodes 243 within the first graphical diagram 240. Each parsing node 243 represents a discrete field 208 of data within the message header 202.

Figure 7:
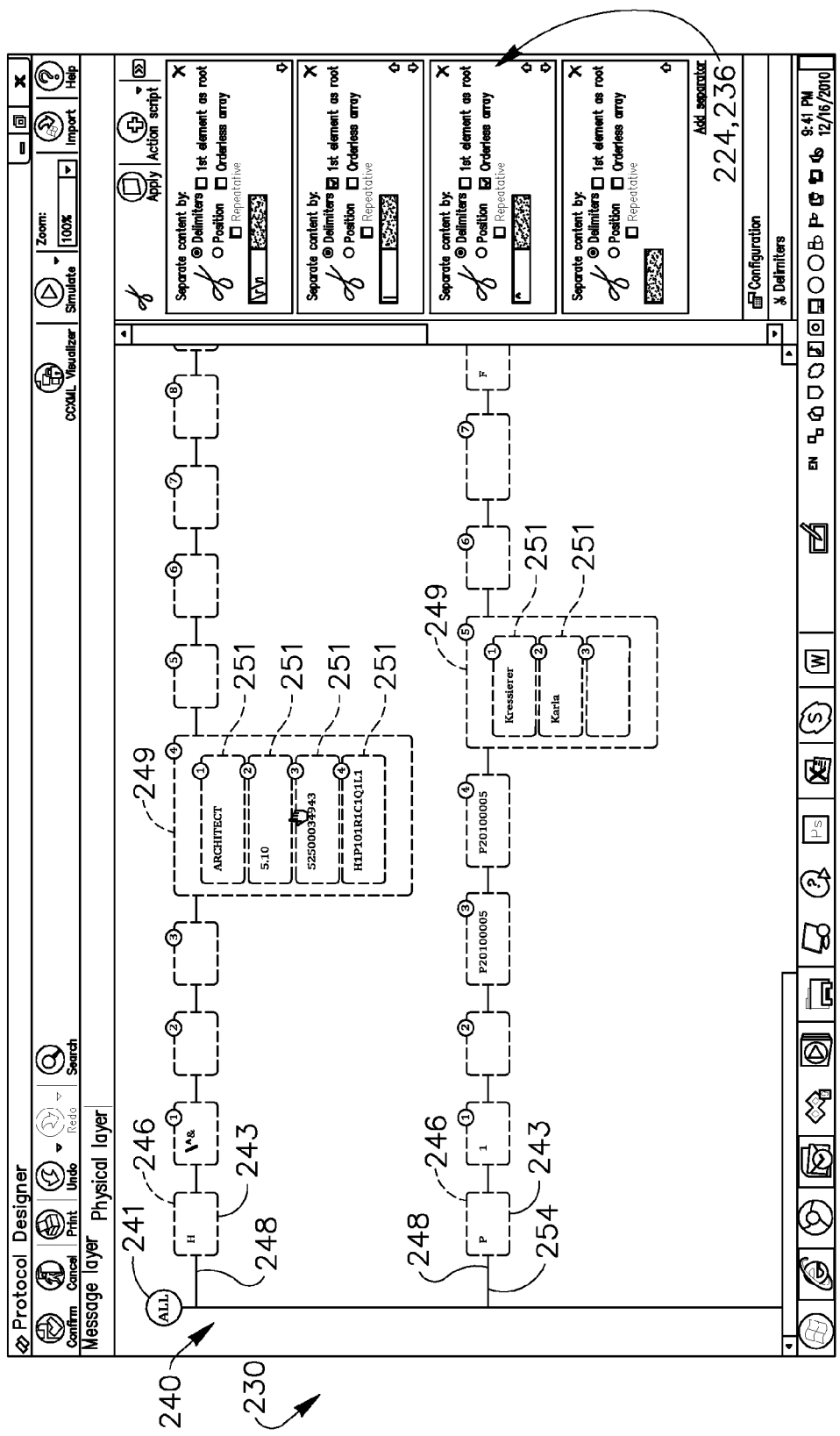

In one embodiment, the third delimiter 236 is a bracket delimiter 224. With reference to FIG. 7, if the third delimiter 236 is a bracket delimiter 224, the hardware message 202 is further delimited into discrete region of text 226 and the driver development module 230 generates in the first graphical program 240 additional embedded parsing nodes 251 for each discrete region of text 226 of the hardware message 202 which is delimited using the third delimiter 236. Each additional embedded parsing node 251 represents a discrete region of text 226 of the hardware message 202 and contains delimiting information on how to separate and delimit the discrete region of text 226 from the hardware message 202. Delimiting information may include the bracket delimiter 224 or bracket delimiters 224 used to delimit the discrete region of text 226 from the hardware message 202.

Moving to block 312, the user continues to input delimiters 206 into the computer readable memory medium 120 until the hardware message 202 is sufficiently or completely delimited. Each delimiter 206 which is input by the user modifies the first graphical diagram 240 and further generates additional parsing nodes 243 or branches 248 within the first graphical diagram 240.

Figure 8:
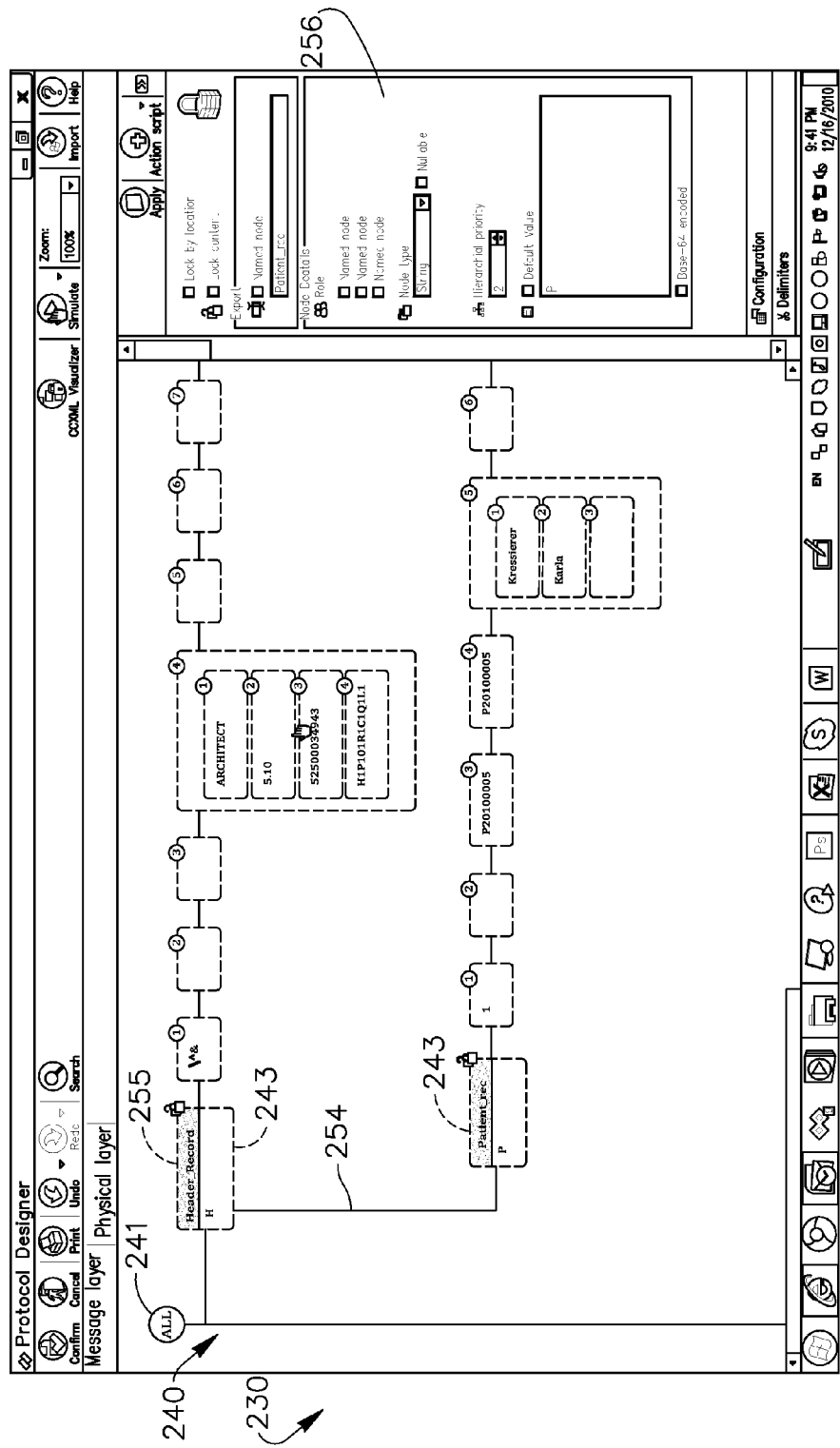
Figure 9:
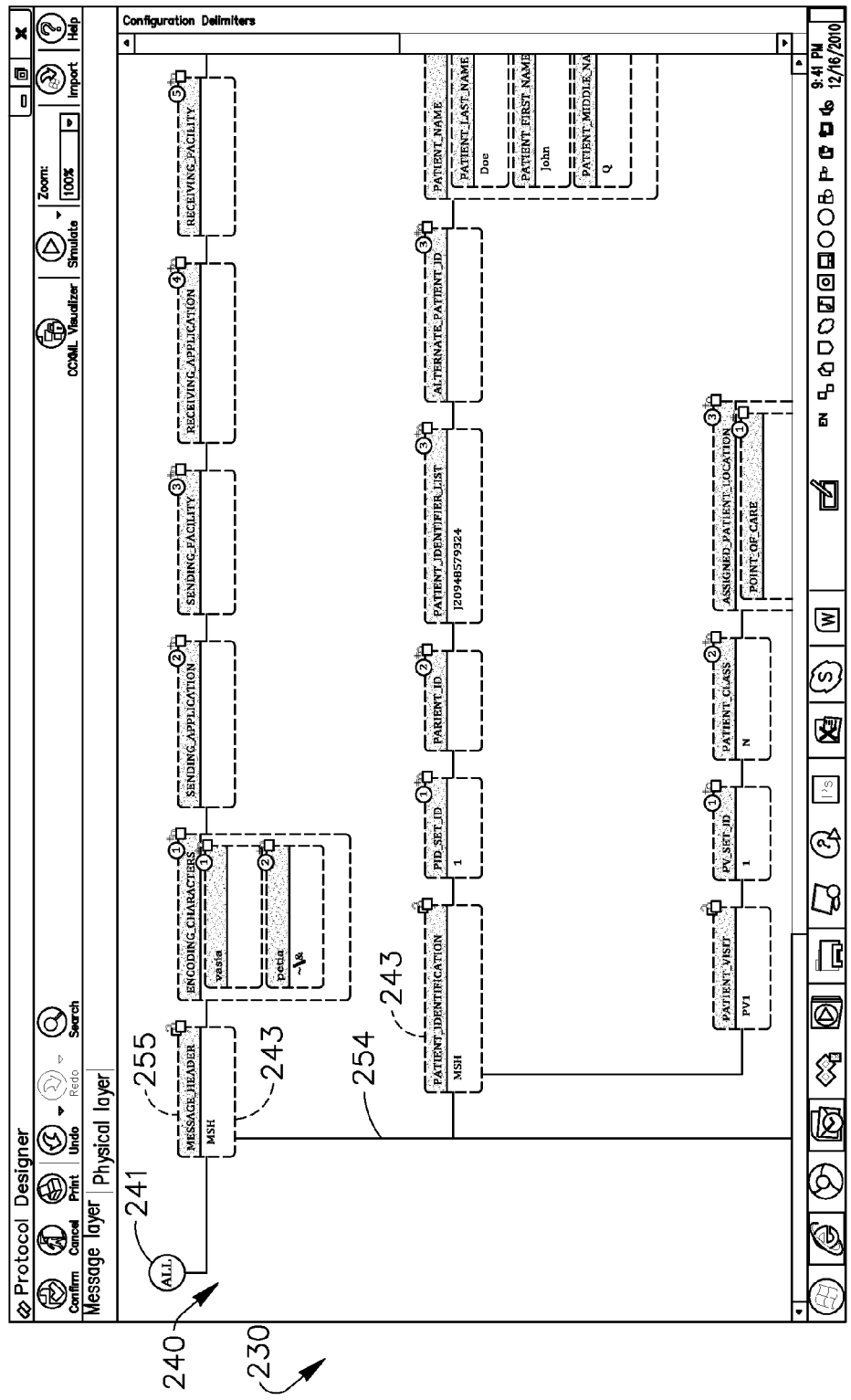

Moving to block 314, if the user has finished delimiting the hardware message, the user may reconfigure the nodes to which branches 248 are connected to. For example, with reference to FIGS. 7, 8, and 9, a secondary branch 254 which originally branched out from and was connected to the root node 241, can be reconfigured by the user to branch out from and connect to a selected node 255.

Moving to block 316, the user may also label each parsing node 243 by selecting a particular node 255, and entering a label within a window 256 or data field within the window 256. Additionally, the user may provide the driver development module with additional information about the selected node 255, such as its hierarchical priority, which indicates its relation to other sections of the hardware message 202, its node type for input validation purposes, and node details such as whether the selected node 255 is a message initiator, a message terminator, or is mandatory or not within the hardware message 202.

Upon generating and configuring the first graphical diagram 240, the method 300 moves to block 318, whereupon the driver development module 230 generates a second graphical diagram 260 in response to user input. The second graphical diagram 260 describes the behavior of the hardware device 200 by mapping out various hardware states of the hardware device by having each unique hardware state represented by state nodes and transitions connecting these state nodes. Each transition defines a hardware condition which must occur for the hardware device 200 to move from one hardware state to another hardware state, and therefore from one state node to another state node.

Figure 10:
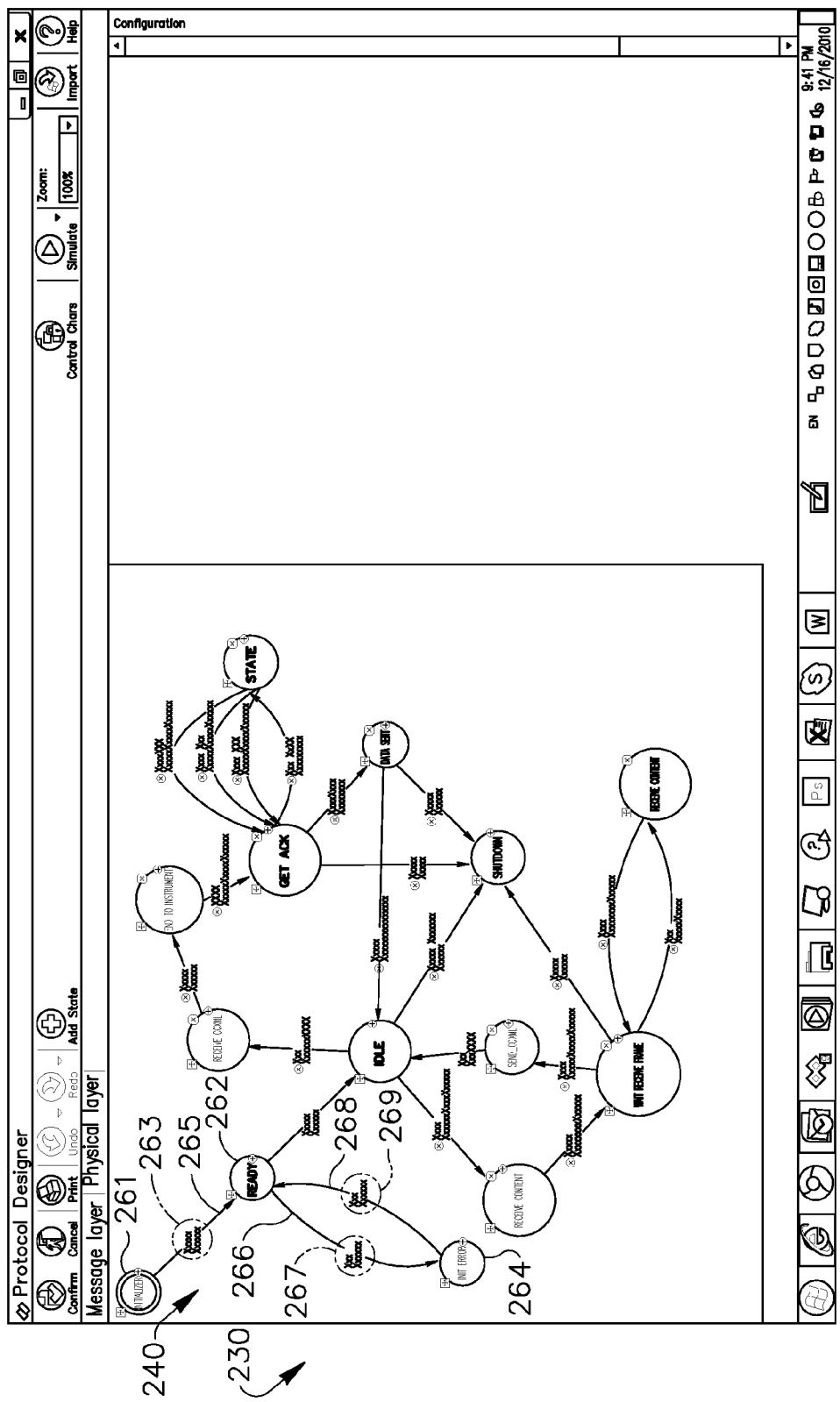
FIG. 10 depicts a second graphical diagram used to generate a connectivity driver, in accordance with one embodiment of the present invention.

The second graphical diagram 260 includes an initializer node 261 which represents a first initialization state in which the hardware device 200 is first turned on. With reference to FIG. 10, user first inserts a first state node 262 into the second graphical diagram 260, at block 320. The first state node 262 is connected with the initializer node 261 through an initialization transition 265 which defines a condition 263 which must be met in order for the hardware device 200 to move from the initialization state represented by the initializer node 261 to a first state represented by the first state node 262.

At block 322, the user then inserts a second state node 264 into the second graphical diagram 260. The second state node 262 is connected with the first state node 262 through a transition 265 which defines a condition 267 which must be met in order for the hardware device 200 to move from the first state represented by the first state node 262 to the second state represented by the second state node 264.

At block 324, the user then inserts a transition 268 connecting the second state node 264 to another state node, such as the first state node 262. The transition 268 defines a condition 269 which must be met in order for the hardware device 200 to move from the second state represented by the second state node 264 to another state, such as the first state represented by the first state node 262.

At block 326, the user proceeds to continue inserting state nodes representing unique hardware states and transitions having conditions which must be met to move from one hardware state, represented by a state node, to another hardware state, represented by another state node. Once the user is finished describing the behavior of the hardware device 200, and has inserted enough state nodes to sufficiently or completely describes the behavior of the hardware device, the second graphical diagram 260 is considered completed.

Upon completion, of the second graphical diagram 260, the driver development module 230 may be prompted to convert the first graphical diagram 240 and the second graphical diagram 260 into program code through which the connectivity driver 218 operates at block 328, and the method 300 then ends at block 330. By automatically converting the first graphical diagram 240 and the second graphical diagram 260 into program code, a simplified method for developing a connectivity driver 218 which does not require the use of a software engineer is provided. This simplified method for developing the connectivity driver 218 allows an end-user who is not a skilled software engineer to develop program code for a connectivity driver 218.

Figure 11:
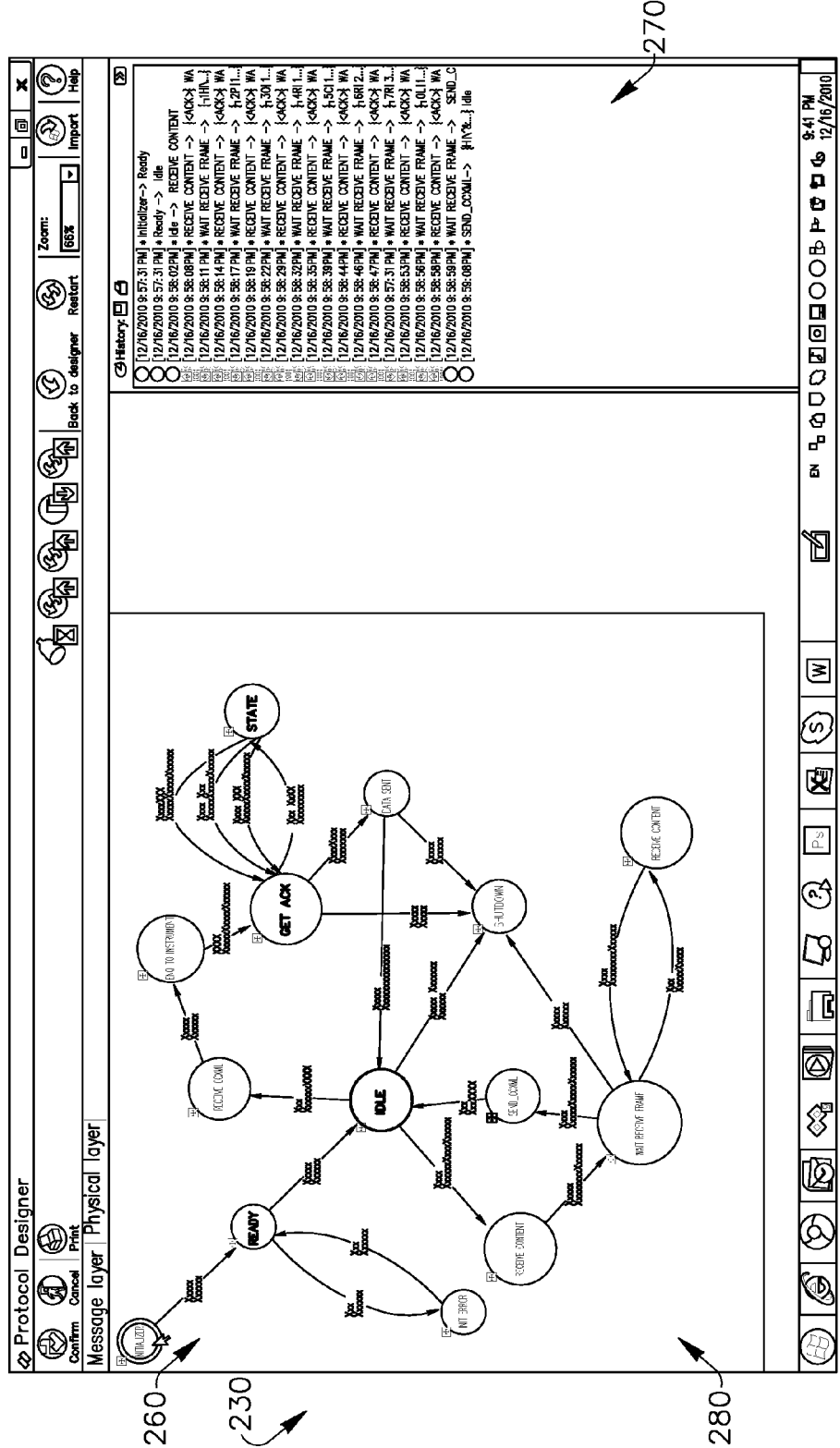
FIG. 11 depicts a simulation of the connectivity driver using the second graphical diagram, in accordance with one embodiment of the present invention.

In one embodiment, the operation of the connectivity driver 218 may be simulated by running a simulation 280 using the second graphical diagram 260 and a virtual hardware device or a real hardware device 200. The virtual hardware device is a computer program representation of the hardware device 200 and generates hardware messages 202 along with providing hardware state information to the driver development module 230, which may be used to simulate the connectivity driver 218 in operation. With reference to FIG. 11, hardware state information generated by the virtual hardware device or the real hardware device 200 is provided to the driver development module 230 and logged in a window 270. As each discrete piece of hardware state information is provided to the driver development module 230, the current state is illustrated by highlighting within the second graphical diagram 260 the respective state node representing the current state. As additional discrete pieces of hardware state information is provided to the driver development module 230, the current state is constantly illustrated by highlighting within the second graphical diagram 260 the respective state node representing the current state. Any state for which no state node is provided or any error in the second graphical diagram 260 will become apparent upon running the simulation 280.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats.

However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a computer readable memory medium such as a magnetic medium like a floppy disk, a hard disk drive, and magnetic tape; an optical medium like a Compact Disc (CD), a Digital Video Disk (DVD), and a Blu-ray Disc; computer memory like random access memory (RAM), flash memory, and read only memory (ROM); and a transmission type medium such as a digital and/or an analog communication medium like a fiber optic cable, a waveguide, a wired communications link, and a wireless communication link.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. Accordingly, the invention is not to be restricted except in light of the appended claims and their equivalents.

The invention claimed is:

1. A non-transitory computer readable memory medium comprising program instructions for graphically developing a connectivity driver, wherein the program instructions are executable by a processor to:
   assemble a first graphical diagram in response to user input, wherein the first graphical diagram represents a parsing sequence for analyzing and converting a hardware message sent using a hardware protocol into software data having a file format readable by a computer program, wherein the entire parsing sequence defines a hardware grammar used to encode and decode discrete fields into and from the hardware message, wherein the first graphical diagram includes:
      a first branch having a primary parsing node, wherein the primary parsing node represents a discrete record field within the hardware message and contains information on how to separate the discrete record field from the hardware message;
   assemble a second graphical diagram in response to user input, wherein the second graphical diagram includes:
      a first state node and a second state node, wherein the first state node is connected with the second state node via a transition, wherein each state node represents a unique hardware state of the hardware device, and the transition includes a transition condition required to move from the first state to the second state, wherein the second graphical diagram maps out various states of the hardware device; and
   convert the first and second graphical diagrams into program code from which the connectivity driver is executed.

2. The non-transitory computer readable memory medium of claim 1, wherein the file format is Extensible Markup Language.

3. The non-transitory computer readable memory medium of claim 1, wherein the computer program is a middleware program, a LIS, or a LIMS.

4. The non-transitory computer readable memory medium of claim 1 further comprising program instructions executable by a processor to parse the hardware message and generate the first branch having the primary parsing node when the user inputs a first delimiter.

5. The non-transitory computer readable memory medium of claim 1 further comprising program instructions executable by a processor to simulate operation of the connectivity driver using the second graphical diagram and a virtual hardware device.

6. The non-transitory computer readable memory medium of claim 1, wherein the discrete record field contains a first plurality of discrete data fields within the hardware message.

7. The non-transitory computer readable memory medium of claim 6 further comprising program instructions executable by a processor to further parse the discrete record field and divide the primary parsing node into a plurality of secondary parsing nodes within the first branch when the user inputs a second delimiter, wherein each secondary parsing node represents a discrete data field within the discrete record field and contains information on how to separate each discrete data field from the discrete record field.

8. The non-transitory computer readable memory medium of claim 1, wherein the hardware message is intended to be communicated from a hardware device to the computer program.

9. The non-transitory computer readable memory medium of claim 1 further comprising program instructions executable by a processor to display the first and second graphical diagrams.

10. The non-transitory computer readable memory medium of claim 1, wherein the parsing sequence may also be used for analyzing and converting software data in a file format to a hardware message sent using a hardware protocol readable by a hardware device.

11. A method for graphically developing a connectivity driver, comprising:
   inputting a hardware message having a stream of data into a non-transitory computer readable memory medium, wherein the hardware message has a first delimiter for demarking the boundary of a discrete record field within the hardware message;
   inputting the first delimiter into the computer readable memory medium;
   accessing the computer readable memory medium and generating, using a processor, a first graphical diagram in response to the inputting of the first delimiter, wherein the graphical diagram includes:
      a first branch having a primary parsing node, wherein the first branch represents the discrete record field within the hardware message, and wherein the primary parsing node represents the discrete record field within the hardware message and contains information on how to separate the discrete record field from the hardware message;
   graphically assembling a second graphical diagram in response to user input, wherein the second graphical diagram includes:
      a first state node and a second state node, wherein the first state node is connected with the second state node via a transition, wherein each state node represents a unique hardware state of the hardware device, and the transition includes a transition condition required to move from the first state to the second state, wherein the second graphical diagram maps out various states of the hardware device; and
   converting the first and second graphical diagrams into program code from which the connectivity driver is executed.

12. The method of claim 11 further comprising:
   inputting a second delimiter into the computer readable memory medium, wherein the hardware message uses the second delimiter for demarking the boundary of a discrete data field within the discrete record field;
   accessing the computer readable memory medium and dividing, using the processor, the primary parsing node into a plurality of secondary parsing nodes within the first branch, wherein each secondary parsing node represents a discrete data field within the discrete record field and contains information on how to separate each discrete data field from the discrete record field.

13. The method of claim 11 wherein the first graphical diagram represents a parsing sequence for analyzing and converting a hardware message sent using a hardware protocol into software data having a file format readable by a computer program.

14. The method of claim 13, wherein the file format is Extensible Markup Language.

15. The method of claim 13, wherein the computer program is a middleware program, a LIS, or a LIMS.

16. The method of claim 11 further comprising simulating operation of the connectivity driver using the second graphical diagram and a virtual hardware device.

17. A laboratory information management system including a module for graphically developing a connectivity driver, comprising:
   a non-transitory computer readable memory medium; and
   at least one processor operable to access from the computer readable memory medium program instructions executable by the processor to:
   assemble a first graphical diagram in response to user input, wherein the first graphical diagram represents a parsing sequence for analyzing and converting a hardware message sent using a hardware protocol into software data having a file format readable by a computer program, wherein the entire parsing sequence defines a hardware grammar used to encode and decode discrete fields into and from the hardware message, wherein the first graphical diagram includes:
      a first branch having a primary parsing node, wherein the primary parsing node represents a discrete record field within the hardware message and contains information on how to separate the discrete record field from the hardware message; and
   assemble a second graphical diagram in response to user input, wherein the second graphical diagram includes:
      a first state node and a second state node, wherein the first state node is connected with the second state node via a transition, wherein each state node represents a unique hardware state of the hardware device, and the transition includes a transition condition required to move from the first state to the second state, wherein the second graphical diagram maps out various states of the hardware device.

18. The system of claim 17, wherein the at least one processor is operable to access from the computer readable memory medium program instructions executable by the processor to convert the first and second graphical diagrams into program code from which the connectivity driver is executed.

19. The system of claim 17, wherein the at least one processor is operable to access from the computer readable memory medium program instructions executable by the processor to parse the hardware message and generate the first branch having the primary parsing node when the user inputs a first delimiter.

20. The system of claim 17, wherein the at least one processor is operable to access from the computer readable memory medium program instructions executable by the processor to simulate operation of the connectivity driver using the second graphical diagram and a virtual hardware device.

* * * * *